United States Patent [19]
Ju et al.

[11] Patent Number: 5,592,956
[45] Date of Patent: Jan. 14, 1997

[54] COMPOSITION AND METHOD FOR INHIBITING THE DESIRE FOR TOBACCO

[75] Inventors: Wei Ju, New York; Morris J. Westfried, Brooklyn; Frank J. Robilotto, New York, all of N.Y.

[73] Assignee: Herbs for Health, Inc., New York, N.Y.

[21] Appl. No.: 497,808

[22] Filed: Jul. 3, 1995

[51] Int. Cl.⁶ ..................................................... A24F 47/00
[52] U.S. Cl. ............................................. 131/270; 514/813
[58] Field of Search .............................. 514/813; 131/270

[56] References Cited

U.S. PATENT DOCUMENTS

| 4,255,439 | 3/1981 | Cooper | 131/270 X |
|---|---|---|---|
| 4,778,677 | 10/1988 | Ebbesen | 514/813 X |
| 4,940,585 | 7/1990 | Hapworth et al. | 514/813 X |
| 4,966,164 | 10/1990 | Colsen et al. | 131/270 X |
| 5,130,132 | 7/1992 | Badmajew | 131/270 X |

*Primary Examiner*—Jennifer Bahr
*Attorney, Agent, or Firm*—Jordan B. Bierman; Bierman and Muserlian

[57] ABSTRACT

A mixture of oil of cloves, oil of wintergreen, monosodiumglutamate, extract of evodia fruit, and extract of Sichuan Lovage Rhizome is applied to certain specific acupuncture points on the human body. As a result of such application, the desire for tobacco is reduced or eliminated and, if use of tobacco is attempted, unpleasant reactions, such as nausea, headaches, dizziness, and vomiting, are experienced.

7 Claims, No Drawings

COMPOSITION AND METHOD FOR INHIBITING THE DESIRE FOR TOBACCO

The present Invention is directed to a composition and method which assists tobacco users in breaking the habit. While portions of this Specification may be expressly directed to smoking, it is to be understood that the method and composition set forth herein are applicable to other forms of tobacco use, such as chewing.

BACKGROUND OF THE INVENTION

As a result of various scientific studies, as well as official and semi-official pronouncements, the dangers of tobacco use have been brought home rather emphatically. As a result, many long-time tobacco users are trying to quit. Various psychological approaches have been tried, including mental therapy, hypnotism, etc. In spite of the foregoing, the percentage of failures and recidivism is relatively high. Therefore, there is a need for something which will reduce the craving for tobacco and assist smokers in ceasing their use thereof.

SUMMARY OF THE INVENTION

It is, therefore, an object of the present Invention to provide a composition which, when introduced into the body, lessens or eliminates the desire for tobacco. It is a further object of the present Invention to provide a composition which, if the user does take a cigarette, will cause the taste of the smoke to be unpleasant and even, in extreme cases, cause nausea, headaches, dizziness, and vomiting.

The present Invention is directed toward the foregoing objects. It resides in a combination of traditional Chinese herbal medicine and acupuncture. More specifically, a particular combination of natural ingredients is placed on the skin at certain specified acupuncture points. As a result, sometimes in a matter of hours, the desire to smoke is minimized and, if tobacco is used, the reaction of the body is extremely unpleasant e.g. nausea, headaches, dizziness, and vomiting.

DETAILED DESCRIPTION OF THE INVENTION

All percentages set forth in this Specification and Claims are by weight. The composition of the present Invention comprises 10% to 45% oil of cloves 2% to 10% oil of wintergreen 22% to 35% monosodiumglutamate 5% to 30% extract of evodia fruit 3% to 25% extract of Sichuan Lovage Rhizome The foregoing ingredients need not be added as such; for example, cloves, evodia fruit, and Sichuan Lovage Rhizome (preferably powdered) can be used in place of the oil of cloves, extract of evodia fruit, and extract of Sichuan Lovage Rhizome, respectively. Of course, the amounts used are adjusted to provide the foregoing concentrations of active ingredients.

The inventive composition can be mixed with any carrier which does not adversely affect the action of the named ingredients. A blend consisting of 35% to 40% beeswax and 15% to 20% mineral oil (based on the total mixture) has been found to be a particularly useful vehicle into which the composition of the present Invention can be incorporated to form a mixture.

The mixture is applied to the human body, preferably over a period of two weeks, at certain acupuncture points; in particular, one or more of Feishu Point, Jingqu Point, Taiyuan Point, Shenmen Point, Kidney Point, and Lung Point. The form of the mixture is not critical, but pellets and semi solids have been found to be particularly suitable. Advantageously, the composition is formed into pellets weighing 0.2 g to 3.0 g (0.08 g to 1.5 g of active ingredients); if appropriate, the mixture may be held in position against the skin by an adhesive tape. Each pellet is preferably held on the skin for about two to three days and then replaced.

It has also been found that rubbing the mixture while on the skin increases its activity. Thus, if a strong craving for tobacco is felt, rubbing the mixture will often give sufficient relief so that the actual use of tobacco is avoided.

EXAMPLE

A composition comprising 35% pulverized cloves, 5% oil of wintergreen, 25% monosodium glutamate, 20% pulverized evodia fruit, and 15% pulverized sichuan lovage rhizome is prepared by blending the ingredients in a container. The carrier, consisting of a blend of beeswax and mineral oil, is added to the composition and the composition and blend are thoroughly mixed to form the final mixture. The mixture, containing 50% carrier, is pressed into pellets, each weighing approximately 2 grams.

While only a single specific embodiment of the present Invention has been expressly disclosed, it is, nonetheless, to be broadly construed, and not to be limited except by the character of the claims appended hereto.

What we claim is:

1. A method of decreasing desire for chewing or smoking tobacco comprising topical application of a composition containing, by weight 10% to 45% oil of cloves 2% to 5% oil of wintergreen 22% to 35% monosodiumglutamate 5% to 30% extract of evodia fruit 3% to 25% extract of Sichuan Lovage Rhizome said composition being applied to at least one acupuncture point selected from the group consisting of Feishu Point, Jingqu Point, Taiyuan Point, Shenmen Point, Kidney Point, and Lung Point.

2. The method of claim 1 wherein said composition comprises about 35% cloves, 5% oil of wintergreen, 25% monosodiumglutamate, 20% evodia fruit, and 15% Sichuan Lovage Rhizome.

3. The method of claim 1 wherein 0.08 g to 1.5 g of said composition is applied to the skin.

4. The method of claim 3 wherein said composition is applied to the skin for about two to three days.

5. The method of claim 1 wherein said application is for up to three weeks.

6. The method of claim 5 wherein said application is for about two weeks.

7. A composition comprising, by weight

10% to 45% oil of cloves

2% to 5% oil of wintergreen

22% to 35% monosodiumglutamate

5% to 30% extract of evodia fruit

3% to 25% extract of Sichuan Lovage Rhizome.

* * * * *